United States Patent [19]

Hearn et al.

[11] Patent Number: 5,599,997
[45] Date of Patent: Feb. 4, 1997

[54] PROCESS FOR THE PRODUCTION OF CYCLOHEXYL AMINE

[75] Inventors: Dennis Hearn; Speros P. Nemphos, both of Pasadena, Tex.

[73] Assignee: Chemical Research & Licensing Company, Pasadena, Tex.

[21] Appl. No.: 404,095

[22] Filed: Mar. 14, 1995

[51] Int. Cl.$^6$ ................................................. C07C 209/72
[52] U.S. Cl. ......................................................... 564/450
[58] Field of Search ............................................. 564/450

[56] References Cited

U.S. PATENT DOCUMENTS

| | | | |
|---|---|---|---|
| 2,373,501 | 4/1945 | Peterson | 260/667 |
| 3,912,787 | 10/1975 | Nowack et al. | 260/667 |
| 3,931,345 | 1/1976 | Gryaznov et al. | 260/667 |
| 4,108,912 | 8/1978 | Takemura et al. | 260/667 |
| 4,197,415 | 4/1980 | Hideyuki et al. | 585/23 |
| 4,225,418 | 9/1980 | Hilfman | 208/111 |
| 4,228,312 | 10/1980 | Noltes et al. | 585/250 |
| 4,232,177 | 11/1980 | Smith | 585/324 |
| 4,327,234 | 4/1982 | Nowack et al. | 585/267 |
| 4,409,411 | 10/1983 | Pez | 585/275 |
| 4,731,496 | 3/1988 | Hu et al. | 585/270 |
| 4,914,239 | 4/1990 | Kiyuma et al. | 564/450 |
| 5,003,118 | 3/1991 | Low et al. | 585/253 |
| 5,087,780 | 2/1992 | Arganbright | 585/259 |
| 5,189,233 | 2/1993 | Larkin et al. | 585/265 |
| 5,210,333 | 5/1993 | Bellows et al. | 585/827 |
| 5,210,348 | 5/1993 | Hsieh et al. | 585/253 |
| 5,246,567 | 9/1993 | Buttke et al. | 208/49 |
| 5,254,763 | 10/1993 | Gill et al. | 585/269 |
| 5,264,641 | 11/1993 | Borghard et al. | 585/269 |
| 5,266,546 | 11/1993 | Hearn | 502/300 |

FOREIGN PATENT DOCUMENTS 0552070  7/1993  European Pat. Off. .

*Primary Examiner*—Brian M. Burn
*Attorney, Agent, or Firm*—Kenneth H. Johnson

[57] ABSTRACT

A process for the hydrogenation of aniline to produce cyclohexyl amine is disclosed wherein the reaction is carried out in a distillation column reactor at a hydrogen partial pressure in the range of 0.1 psia to less than 100 psia. The catalyst is prepared in the form of a catalytic distillation structure. Within the distillation reaction zone there is an internal reflux and liquid from an external reflux which cool the rising vaporous aniline condensing a portion within the bed.

14 Claims, 1 Drawing Sheet

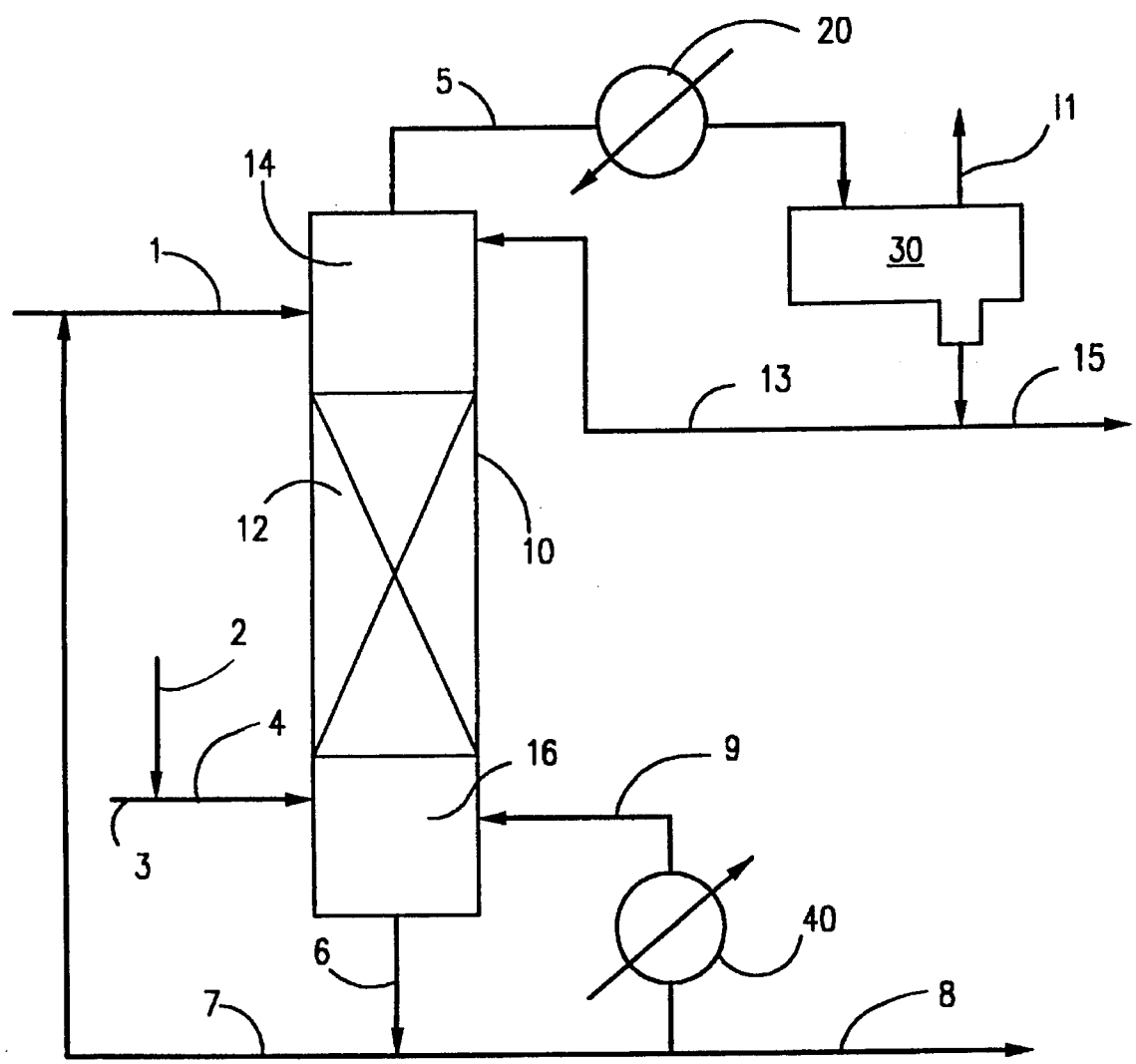

PROCESS FOR THE PRODUCTION OF CYCLOHEXYL AMINE

BACKGROUND OF THE INVENTION

1. Field of the Invention

The present invention relates to the a process for the production of cyclohexyl amine by hydrogenation of aniline. More particularly the invention relates to a process wherein the hydrogenation of aniline is carried out in a distillation column reactor having a condensing component in the reaction section of the column.

2. Related Information

Cyclohexyl amine has been produced by a number of processes in the past including amination of cyclohexanol and the hydrogenation of aniline. The major difficulty encountered in the hydrogenation of aniline is the formation of varying amounts of dicyclohexyl amine byproduct.

Catalyst known to promote the hydrogenation of aniline are metals in Group VIII of the periodic table. In the past the proclivity to produce dicyclohexyl amine is rated from the least likely to the most likely as Ruthenium rhodium<palladium=platinum. Supports used for the metals are carbon, barium carbonate, alumina, barium sulfate and calcium carbonate. The supports also affect the production of dicyclohexyl amine in the order carbon>barium carbonate>alumina>barium sulfate>calcium carbonate.

SUMMARY OF THE INVENTION

The present invention uses catalytic distillation in the hydrogenation of aniline to take advantage of the condensing distillate within the distillation reaction zone in the distillation column reactor. Actual separation may only be a secondary consideration. The operation of the distillation column reactor results in both a liquid and vapor phase within the distillation reaction zone. A considerable portion of the vapor is hydrogen and ammonia while a portion is vaporous aniline. Within the distillation reaction zone there is an internal reflux and liquid from an external reflux which cool the rising vaporous aniline condensing a portion within the bed.

Without limiting the scope of the invention it is proposed that the mechanism that produces the effectiveness of the present process is the condensation of a portion of the vapors in the reaction system, which occludes sufficient hydrogen in the condensed liquid to obtain the requisite intimate contact between the hydrogen and the aniline in the presence of the catalyst to result in its hydrogenation to cyclohexyl amine.

The process can thus be considered to comprise:

(a) feeding a first stream containing aniline and a second stream containing hydrogen to a distillation column reactor;

(b) contacting the aniline and hydrogen at a hydrogen partial pressure in the range of about 0.1 psig to less than 150 psig, preferably less than 100 psig, in the presence of a hydrogenation catalyst prepared in the form of a catalytic distillation structure thereby reacting a portion of the aniline with a portion of the hydrogen to form a reaction mixture containing cyclohexyl amine, unreacted hydrogen and unreacted aniline;

(b) maintaining the pressure in the distillation column reactor such that the reaction mixture is at its boiling point;

(c) removing gaseous aniline, gaseous cyclohexyl amine and hydrogen as overheads from the distillation column reactor;

(d) condensing substantially all of the aniline and cyclohexyl amine removed as overheads from the distillation column reactor;

(e) returning a portion of the condensed aniline and cyclohexyl amine to the distillation column reactor as reflux; and (f) withdrawing an overheads liquid product containing cyclohexyl amine from the distillation column.

BRIEF DESCRIPTION OF THE DRAWING

The FIGURE is flow diagram in schematic form of one embodiment of the present invention.

DESCRIPTION OF THE PREFERRED EMBODIMENT

Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

As described the catalytic material employed in the hydrogenation process is in a form to serve as distillation packing. Broadly stated, the catalytic material is a component of a distillation system functioning as both a catalyst and distillation packing, i.e., a packing for a distillation column having both a distillation function and a catalytic function.

The reaction system can be described as heterogenous since the catalyst remains a distinct entity. Any suitable hydrogenation catalyst may be used, for example Group VIII metals of the Periodic Table of Elements as the principal catalytic component, alone or with promoters and modifiers such as palladium/gold, palladium/silver, cobalt/zirconium, nickel preferably deposited on a support such as alumina, fire brick, pumice, carbon, silica, resin or the like.

A preferred catalyst structure for the hydrogenation of aniline comprises at least one plurality of flexible, semi-rigid open mesh tubular elements filed with a particulate catalytic material (catalyst component) and sealed at both ends, intimately associated with and supported by a wire mesh screen coiled into a spiral having a longitudinal axis, said tubular element being arrayed at an angle to the longitudinal axis thereby forming a bale and is described in detail in U.S. patent application Ser. No. 08/188,803 filed Jan. 31, 1994 (now U.S. Pat. No. 5,431,890) incorporated herein. Such individual elements are similar in appearance to link "sausages".

The flexible, semi-rigid open mesh tubular element filled with a particulate catalytic material preferably has a fastener every 1–12 inches along the length of the tube to form a multiple link shaped catalytic distillation structure. The links formed by the fasteners may be evenly or irregularly spaced.

The bale shaped catalytic distillation structures are formed by placing at least one tubular element on top of the wire mesh screen, such as demister wire, in a diagonal array, such that when the wire mesh screen is rolled up, the rolled structure provides a new and improved catalytic distillation structure. Further embodiments include multiple stack arrangements of alternating wire screen mesh and tubular elements that are rolled into a new bale shaped catalytic distillation structure. The tubular elements on alternating layers are preferably arrayed on the wire mesh screen in opposite directions such that their paths cross. Each tubular element will define a spiral within the bale. Other structures known in the art may be used such as disclosed in U.S. Pat. Nos. 4,443,559 and 5,348,710.

The catalyst component may take several forms. In the case of particulate catalytic material, generally from 60 mm to about 1 mm down through powders, is enclosed in a porous container such as screen wire, or polymeric mesh. The material used to make the container must be inert to the reactants and conditions in the reaction system. The screen wire may be aluminum, steel, stainless steel, and the like. The polymer mesh may be nylon, teflon, glass fibers, i.e., silicate polymer or the like having a softening, e.g., melting temperature higher than 400° F., the temperature of the catalyst bed during the reaction. The mesh or threads per inch of the material used to make the container is such that the catalyst is retained therein and will not pass through the openings in the material. Although the catalyst particles of about 0.15 mm size or powders may be used and particles up to about ¼ inch diameter may be employed in the containers.

The hydrogenation of aniline is an exothermic reaction. In the past the temperature has been controlled by quench at strategic points within a reactor by addition of cool hydrogen. The addition of the hydrogen also acted to maintain a molar excess of hydrogen within the reactor to prevent coking and other undesirable side reactions. It is believed that in the present reaction catalytic distillation is a benefit first, because the reaction is occurring concurrently with distillation, the initial reaction products and other stream components are removed from the reaction zone as quickly as possible reducing the likelihood of side reactions. Second, because all the components are boiling the temperature of reaction is controlled by the boiling point of the mixture at the system pressure. The heat of reaction simply creates more boil up, but no increase in temperature at a given pressure.

The present invention carries out the method in a catalyst packed column which can be appreciated to contain a vapor phase and some liquid phase as in any distillation. The distillation column reactor is operated at a pressure such that the reaction mixture is boiling in the bed of catalyst.

The present process operates at overhead pressure of said distillation column reactor in the range between 0 and 300 psig, preferably 200 or most suitable 35 to 120 psig and temperatures in said distillation reaction bottoms zone in the range of 150° to 500° F., preferably 250° to 450° F., e.g. 300° to 400° F. at the requisite hydrogen partial pressures. The feed weight hourly space velocity (WHSV), which is herein understood to mean the unit weight of feed per hour entering the reaction distillation column per unit weight of catalyst in the catalytic distillation structures, may vary over a very wide range within the other condition perimeters, e.g. 0.1 to 35.

In the current process the temperature is controlled by operating the reactor at a given pressure to allow partial vaporization of the reaction mixture. The exothermic heat of reaction is thus dissipated by the latent heat of vaporization of the mixture. The vaporized portion is taken as overheads and a portion of the condensible material condensed and returned to the column as reflux.

The downward flowing liquid causes additional condensation within the reactor as is normal in any distillation. The contact of the condensing liquid within the column provides excellent mass transfer for dissolving the hydrogen within the reaction liquid and concurrent transfer of the reaction mixture to the catalytic sites. It is thought that this condensing mode of operation results in the excellent conversion and selectivity of the instant process and allows the lower hydrogen partial pressures and reactor temperatures noted. A further benefit that this reaction may gain from catalytic distillation is the washing effect that the internal reflux provides to the catalyst thereby reducing polymer build up and coking. Internal reflux may vary over the range of 0.2 to 20 L/D (wt. liquid just below the catalyst bed/wt. distillate) and give excellent results.

Hydrogen must be supplied in at least stoichiometric quantities. The preferred ratio is greater than 4:1 molar ratio of hydrogen to aniline. Ammonia may be provided to suppress the side reactions and promote the production of cyclohexyl amine. The molar ratio of ammonia to aniline is preferably at least 1:1. Hydrogen should be present in the molar ratio of about 4:1 of hydrogen to ammonia.

Referring now to the FIGURE there is shown a flow diagram of one embodiment of the invention. Aniline is fed via line 1 to the distillation column reactor 10 at a point above the catalyst bed 12 containing the catalytic distillation structure. Hydrogen is fed via flow line 2 and ammonia via flow line 3 which are combined in flow line 4 and fed below the bed 12. Overheads containing the cyclohexyl amine and unreacted aniline and hydrogen are taken via flow line 5 and passed through partial condenser 20 wherein the condensible materials are condensed. The overheads are then collected in receiver/separator 30 wherein the hydrogen and other uncondensed vapors, e.g., ammonia, are separated and removed via flow line 11 for recycle (not shown) if desired to the hydrogen feed or at a point below the catalyst bed. Product is taken via flow line 15 and a portion of the condensed overheads is returned to the distillation column reactor 10 as reflux via flow line 13.

Bottoms are taken via flow line 6 and a portion are passed through reboiler 40 to balance heat for the column 10. The bottoms contain heavy by-products which include cyclohexyl phenyl amine and dicyclohexyl amine. A portion of the bottoms may be recycled to the feed via flow line 7 for conversion to cyclohexyl amine. A bottoms draw via flow line 8 is provided to prevent build up of the heavies.

The distillation column reactor is provided with rectifying section 14 to separate unreacted aniline from the product and stripping section 16 to insure that no aniline or product is removed as bottoms.

In the following examples a twenty five foot tall one inch diameter distillation column reactor was used. The catalyst used was Calsicat E-475 SR, 56% nickel on alumina in the form of ³⁄₁₆" spheres. The catalyst was packaged as six inch long by 0.75 inch diameter "sausages" as described above wrapped with 100 mesh stainless steel screen.

EXAMPLE 1

In this example 0.66 pound of the Calsicat E-475 prepared as described above was loaded into the middle 10 feet of the distillation column reactor. The top and bottom 7.5 feet were packed with ceramic saddles. Conditions and results are summarized in Table I below. The data show that pressure (and consequently temperature in the catalyst zone) had the greatest leverage on productivity ranging from –0.15 lbs/lb catalyst at 50 psig to −0.4 lbs/lb at 150 psig. Selectivity to cyclohexyl amine was in the 65–75% range with the main by-products being cyclohexyl phenyl amine and dicyclohexyl amine.

TABLE I

| Time On Stream, Hrs. | 100 | 160 | 210 | 260 |
|---|---|---|---|---|
| Pressure, psig | 50 | 100 | 150 | 50 |
| Temperature, °F. | | | | |
| Overhead | 280 | 300 | 280 | 350 |
| Cat. Bed | 350 | 380 | 400 | 400 |
| Bottoms | 500 | 580 | 620 | 530 |
| Aniline Feed, lbs/hr | 0.4 | 0.4 | 0.6 | 0.5 |
| Overhead, lbs/hr | 0.3 | 0.3 | 0.50 | 0.3 |
| Cyclohexyl amine, wt % | 15 | 25 | 45 | 8 |
| Bottoms, lbs/hr | 0.1 | 0.1 | 0.2 | 0.1 |
| Hydrogen Rate, SCFH | 15 | 15 | 15 | 15 |
| Ammonia, lbs/hr | 0.1 | 0.1 | 0.2 | 0.1 |
| Cyclohexyl Amine Selectivity, wt % | 66 | 71 | 77 | 41 |
| Total Amines Productivity, lbs/hr/lb | 0.11 | 0.23 | 0.4 | 0.12 |

EXAMPLE 2

In this example 1.0 pound of the Calsicat E-475 prepared as described above was loaded into the bottom 15 feet of the distillation column reactor. The top 10 feet were packed with ceramic saddles. Conditions and results are summarized in Table I below. During part of the run (from about 250 hours onward) the heavy bottoms product containing the cyclohexyl phenyl amine and dicyclohexyl amine were recycled at a rate of 20 wt % of the fresh feed.

TABLE II

| Time On Stream, Hrs. | 100 | 200 | 300 |
|---|---|---|---|
| Pressure, psig | 50 | 50 | 50 |
| Aniline Feed, lbs/hr | 0.5 | 0.8 | 0.8 |
| Overhead, lbs/hr | 0.4 | 0.7 | 0.7 |
| Cyclohexyl amine, wt % | | | |
| Bottoms, lbs/hr | 0.1 | 0.1 | 0.1 |
| Hydrogen Rate, SCFH | 15 | 20 | 20 |
| Ammonia, lbs/hr | 0.1 | 0.1 | 0.1 |
| Cyclohexyl Amine Selectivity, wt % | 66 | 72 | 71 |
| Total Amines Productivity, lbs/hr/lb | 0.3 | 0.4 | 0.35 |

The invention claimed is:

1. A process for the production of cyclohexyl amine from the hydrogenation of aniline comprising the steps of:
   (a) feeding a first stream containing aniline and a second stream containing hydrogen to a distillation column reactor above a reaction distillation zone;
   (b) contacting the aniline and hydrogen in a reaction distillation zone containing a hydrogenation catalyst prepared in the form of a catalytic distillation structure and having both a liquid and vapor phase at a hydrogen partial pressure in the range of about 0.1 psia to less than 100 psia, in thereby reacting a portion of the aniline with a portion of the hydrogen to form a reaction mixture containing cyclohexyl amine, unreacted hydrogen and unreacted aniline;
   (c) maintaining the pressure in the distillation column reactor such that the reaction mixture is at its boiling point;
   (d) removing gaseous aniline, gaseous cyclohexyl amine and hydrogen as overheads from the distillation column reactor;
   (e) condensing substantially all of the aniline and cyclohexyl amine removed as overheads from the distillation column reactor;
   (f) returning a portion of the condensed aniline and cyclohexyl amine to the distillation column reactor as reflux; and
   (g) withdrawing an overheads liquid product containing cyclohexyl amine from the distillation column.

2. The process according to claim 1 wherein the vapor product after condensing the overheads is recycled to the distillation reactor with the hydrogen feed or at another place below the catalyst bed.

3. The process according to claim 1 wherein cyclohexyl phenyl amine and dicyclohexyl amine are formed as by-products in the reaction mixture.

4. The process according to claim 3 further comprising the step of feeding a third stream containing ammonia to said distillation column reactor.

5. The process according to claim 4 wherein said cyclohexyl phenyl amine and dicyclohexyl amine are removed from said distillation column reactor as bottoms.

6. The process according to claim 5 wherein a portion of said bottoms are recycled as feed to said distillation column reactor along with said aniline an a portion of the cyclohexyl phenyl amine and dicyclohexyl amine are converted to cyclohexyl amine.

7. The process according to claim 1 wherein the overhead pressure is in the range of 0 to 350 psig.

8. The process according to claim 7 wherein the temperature within catalyst bed is in the range of 150° to 500° F.

9. The process according to claim 1 wherein said catalyst comprises 3/16 inch spheres of nickel on alumina and said catalytic distillation structure comprises at least one plurality of flexible, semi-rigid open mesh tubular elements filled with said spheres and sealed at both ends, intimately associated with and supported by a wire mesh screen coiled into a spiral having a longitudinal axis, said tubular element being arrayed at an angle to the longitudinal axis thereby forming a bale.

10. A process for the production of cyclohexyl amine from the hydrogenation of aniline comprising the steps of:
    (a) feeding to a distillation column reactor a first stream containing aniline at a point above a reaction distillation zone, and below said reaction distillation zone a second stream containing hydrogen and a third stream containing ammonia;
    (b) concurrently in said distillation column reactor
       (i) contacting said aniline, hydrogen and ammonia in the presence of a hydrogenation catalyst prepared in the form of a catalytic distillation structure in a reaction distillation zone having both a vapor and liquid phase, to form a reaction mixture containing cyclohexyl amine product, cyclohexyl phenyl amine and dicyclohexyl amine by-products, unreacted aniline, unreacted hydrogen and unreacted ammonia;
       (ii) distilling said reaction mixture such that there is continuous boiling and condensing of the mixture within said reaction distillation zone;
    (c) removing cyclohexyl amine, unreacted aniline, unreacted hydrogen and unreacted ammonia from said distillation column reactor as overheads;
    (d) condensing substantially all of said cyclohexyl amine and aniline contained in said overheads;
    (e) returning a portion of said condensed cyclohexyl amine and aniline to said distillation column reactor as reflux;

(f) withdrawing said cyclohexyl phenyl amine and dicyclohexyl amine by-products from said distillation column reactor as bottoms; and (g) recycling a portion of said bottoms containing said cyclohexyl phenyl amine and dicyclohexyl amine by-products to said distillation reaction zone for conversion to cyclohexyl amine.

11. The process according to claim 9 wherein the molar ratio of hydrogen to aniline is at least 4:1.

12. The process according to claim 10 wherein the vapor product after condensing the overheads is recycled to the distillation reactor with the hydrogen feed or at another place below the catalyst bed.

13. The process according to claim 12 wherein the molar ratio of hydrogen to ammonia is about 4:1.

14. The process according to claim 10 wherein the molar ratio of ammonia to aniline is at least 1:1.

* * * * *